United States Patent
Oode et al.

(10) Patent No.: US 11,166,642 B2
(45) Date of Patent: Nov. 9, 2021

(54) MEASUREMENT SENSOR PACKAGE AND MEASUREMENT SENSOR

(71) Applicant: KYOCERA Corporation, Kyoto (JP)

(72) Inventors: Yasushi Oode, Kirishima (JP); Hiroki Ito, Kirishima (JP); Yoshimasa Sugimoto, Kirishima (JP); Noritaka Niino, Kirishima (JP); Shogo Matsunaga, Kirishima (JP); Takuya Hayashi, Kirishima (JP)

(73) Assignee: KYOCERA CORPORATION, Kyoto (JP)

( * ) Notice: Subject to any disclaimer, the term of this patent is extended or adjusted under 35 U.S.C. 154(b) by 651 days.

(21) Appl. No.: 15/770,658

(22) PCT Filed: Nov. 10, 2016

(86) PCT No.: PCT/JP2016/083435
§ 371 (c)(1),
(2) Date: Apr. 24, 2018

(87) PCT Pub. No.: WO2017/110291
PCT Pub. Date: Jun. 29, 2017

(65) Prior Publication Data
US 2018/0310836 A1 Nov. 1, 2018

(30) Foreign Application Priority Data
Dec. 22, 2015 (JP) .............................. JP2015-250656

(51) Int. Cl.
*A61B 5/026* (2006.01)
*H01L 23/60* (2006.01)
*A61B 5/00* (2006.01)

(52) U.S. Cl.
CPC ............ *A61B 5/0261* (2013.01); *A61B 5/026* (2013.01); *A61B 5/6826* (2013.01); *H01L 23/60* (2013.01); *A61B 2562/182* (2013.01)

(58) Field of Classification Search
CPC . A61B 2562/182; A61B 5/0261; A61B 5/026; A61B 5/6826;
(Continued)

(56) References Cited

U.S. PATENT DOCUMENTS 6,084,295 A * 7/2000 Horiuchi ................. H01L 24/48
257/690
6,486,534 B1 * 11/2002 Sridharan ......... H01L 23/49816
257/659

(Continued)

FOREIGN PATENT DOCUMENTS

JP 5031895 B2 9/2012

*Primary Examiner* — Sean D Mattson
(74) *Attorney, Agent, or Firm* — Volpe Koenig

(57) ABSTRACT

A measurement sensor package and a measurement sensor reduce susceptibility to noise and enable highly accurate measurement. A measurement sensor package (1) includes a substrate (2), a lid (3), and a ground conductor layer (4). The substrate (2) contains a light emitter and a light receiver, and includes a substrate body (20), a plurality of ground via conductors (21), an frame-shaped ground conductor layer (22), signal wiring conductors (23), and an external connection terminal (24). The ground via conductors (21) are connectable to a ground potential, and are located outward from a first recess (20*a*) and a second recess (20*b*) included in the substrate body (20) in a plan view.

13 Claims, 8 Drawing Sheets

(58) Field of Classification Search
CPC ...... A61B 5/0059–0091; A61B 5/1455; A61B 5/02427–02433; A61N 1/14; H05F 3/00; H05F 3/02; H01L 23/60
See application file for complete search history.

(56) References Cited

U.S. PATENT DOCUMENTS

| | | | |
|---|---|---|---|
| 8,199,518 B1* | 6/2012 | Chun | H01L 23/3128 361/767 |
| 2008/0097172 A1* | 4/2008 | Sawada | A61B 5/0261 600/310 |
| 2009/0202251 A1* | 8/2009 | Shibayama | A61B 5/0261 398/138 |
| 2009/0296762 A1* | 12/2009 | Yamaguchi | H04N 9/3161 372/34 |
| 2010/0004519 A1* | 1/2010 | Lamego | A61B 5/02416 600/310 |
| 2011/0092832 A1* | 4/2011 | Onoe | A61B 5/6826 600/504 |
| 2011/0260176 A1* | 10/2011 | Onoe | A61B 5/0261 257/79 |
| 2011/0278703 A1* | 11/2011 | Pagaila | H01L 23/49827 257/659 |
| 2013/0341650 A1* | 12/2013 | Peng | H01L 31/0203 257/82 |

* cited by examiner ized as US 11,166,642 B2

MEASUREMENT SENSOR PACKAGE AND MEASUREMENT SENSOR

FIELD

The present invention relates to a measurement sensor package and a measurement sensor.

BACKGROUND

Measurement sensors that easily and speedily measure biological information including blood flow have been awaited. Measurement of blood flow uses, for example, the Doppler effect of light. When blood is illuminated with light, the light is scattered by blood cells, such as red blood cells. The frequency of the illuminating light and the frequency of the scattered light are used to calculate the traveling speed of the blood cells.

One example of the measurement sensor for measuring blood flow is a self-luminous measurement sensor described in Patent Literature 1. The sensor includes a substrate, an illuminator arranged on the substrate to illuminate blood with light, a light receiver arranged on the substrate to receive scattered light, and a front plate bonded to the substrate with a light-shielding bond surrounding the illuminator and the light receiver.

When measuring blood flow, for example, a fingertip, which is an area to be measured, is placed in contact with the surface of the front plate. The human fingertip functions like a capacitor. When a fingertip touches the measurement sensor, electric charge accumulating in the fingertip is discharged. The discharge of the electric charge causes noise to interfere with a current input into a light emitter and a current output from a light receiver, thus lowering the measurement accuracy.

CITATION LIST

Patent Literature

Patent Literature 1: Japanese Patent No. 5031895

BRIEF SUMMARY

A measurement sensor package according to one aspect of the present invention includes a substrate, a lid, and a ground conductor layer. The substrate includes a substrate body and one or more ground via conductors. The substrate body includes a plurality of dielectric layers stacked on one another, and is a rectangular plate. The substrate body includes a first recess to contain a light emitter and a second recess to contain a light receiver on its first surface. The one or more ground via conductors include a plurality of ground via conductors, and are located outward from the first recess and the second recess included in the substrate body in a plan view. The ground via conductors are connectable to a ground potential. The lid is a plate including an insulating material. The lid covers the first recess and the second recess, and transmits light emitted from the light emitter contained in the first recess and transmits light to be received by the light receiver contained in the second recess. The ground conductor layer is located on a surface facing the first recess and the second recess of the lid, and connectable to a ground potential. The ground conductor layer has a first opening that allows passage of light emitted from the light emitter and a second opening that allows passage of light to be received by the light receiver. The ground conductor layer is electrically connectable to the plurality of ground via conductors.

A measurement sensor according to another aspect of the present invention includes the measurement sensor package according to the above aspect, a light emitter contained in the first recess, and a light receiver contained in the second recess.

BRIEF DESCRIPTION OF DRAWINGS

The objects, features, and advantages of the present invention will become apparent from the following detailed description and the drawings.

DETAILED DESCRIPTION

Figure 1:
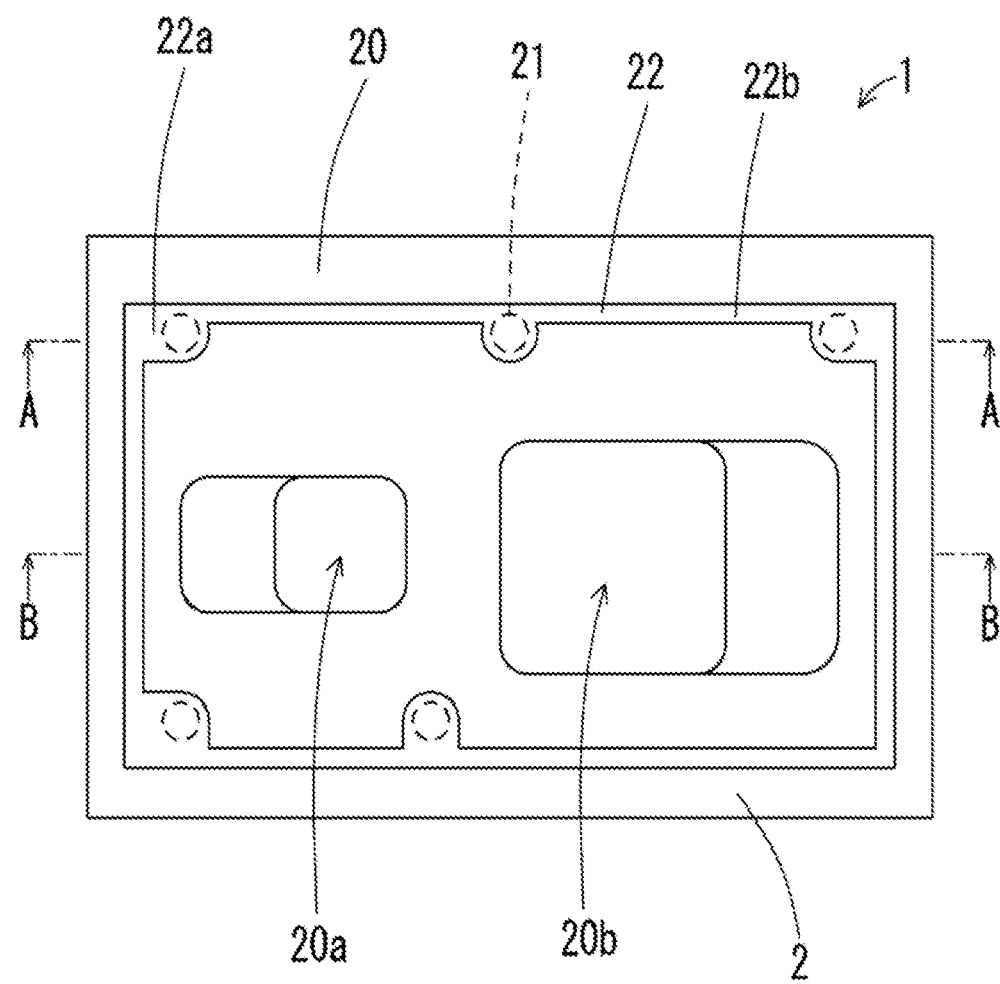
FIG. 1 is a plan view of a measurement sensor package 1 according to an embodiment of the present invention.
Figure 2:
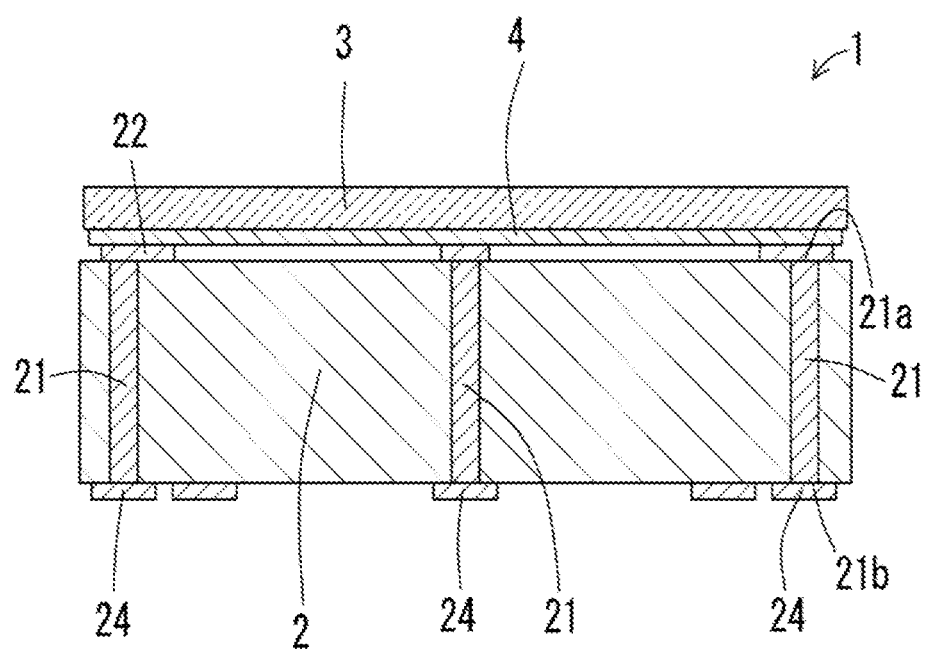
FIG. 2 is a cross-sectional view of the measurement sensor package 1 taken along line A-A of FIG. 1.
Figure 3:
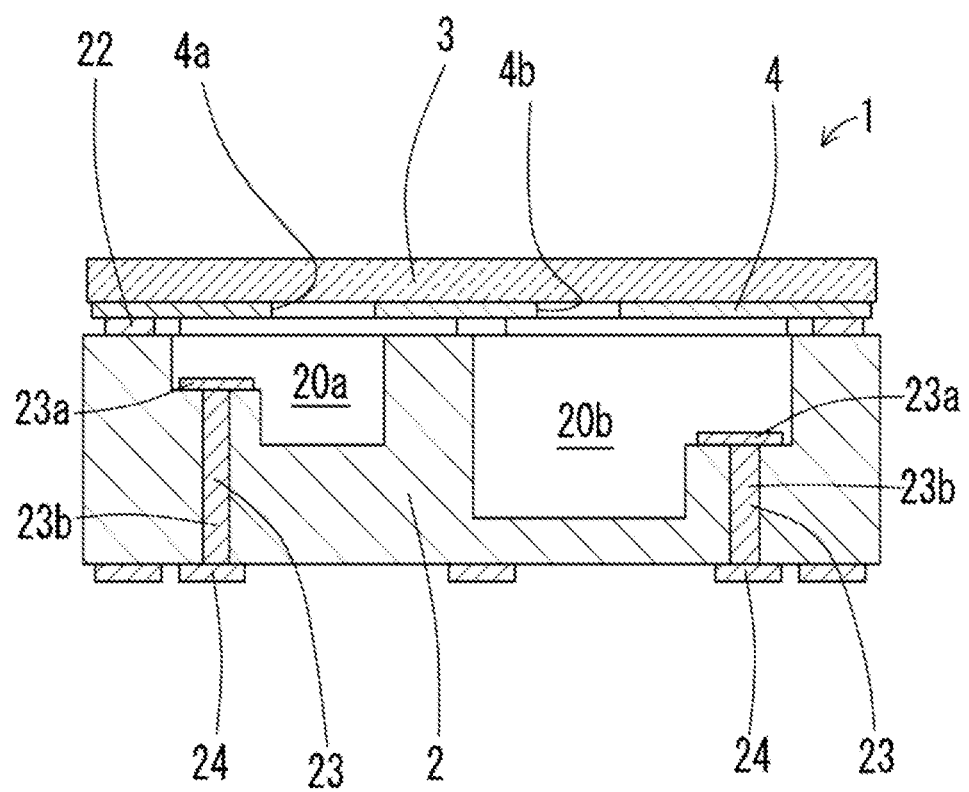
FIG. 3 is a cross-sectional view of the measurement sensor package 1 taken along line B-B of FIG. 1.

FIG. 1 is a plan view of a measurement sensor package 1 according to an embodiment of the present invention. FIG. 2 is a cross-sectional view of the measurement sensor package 1 taken along line A-A of FIG. 1. FIG. 3 is a cross-sectional view of the measurement sensor package 1 taken along line B-B of FIG. 1. In the plan view of FIG. 1, a lid 3 is not shown.

The measurement sensor package 1 includes a substrate 2, the lid 3, and a ground conductor layer 4. The substrate 2 contains a light emitter and a light receiver. The substrate 2 includes a substrate body 20, multiple ground via conductors 21, an frame-shaped ground conductor layer 22, signal wiring conductors 23, and external connection terminals 24.

The substrate body 20 according to the present embodiment is a rectangular plate, and includes multiple dielectric layers stacked on one another. The substrate body 20 has at least two recesses, which are a first recess 20a for containing a light emitter, and a second recess 20b for containing a light receiver. The first recess 20a and the second recess 20b are open in the same first surface (one main surface) of the substrate body 20.

The measurement sensor package 1 in the present embodiment may be used for a measurement sensor that measures fluid flow such as blood flow using the Doppler effect of light. To use the Doppler effect of light, the measurement sensor includes a light emitter, which illuminates an object to be measured with light, and a light receiver, which receives light scattered by the object. When measuring, for example, blood flow, the measurement sensor package 1 illuminates a body part, such as a finger, with external light, and receives light scattered at blood cells in the blood flowing through blood vessels under the skin to measure the blood flow based on changes in the frequency. Thus, the light emitter and the light receiver are arranged at a predetermined distance from each other in the measurement sensor package 1 based on the positional relationship between the illumination light and the scattering light. The first recess 20a and the second recess 20b are located in accordance with the positional relationship between the light emitter and the light receiver.

The first recess 20a and the second recess 20b may be sized in accordance with the size of the light emitter and the size of the light receiver to be contained in the recesses. When, for example, a vertical cavity surface emitting laser (VCSEL) element is used as the light emitter, the first recess 20a may have a rectangular opening or a square opening. The opening of the first recess 20a has a vertical dimension of, for example, 0.3 to 2.0 mm, and a horizontal dimension of 0.3 to 2.0 mm. The first recess 20a has a depth of 0.3 to 1.0 mm. Also, when a surface incident photodiode is used as the light receiver, the second recess 20b may have a rectangular opening or a square opening. The opening of the second recess 20b has a vertical dimension of, for example, 0.3 to 2.0 mm, and a horizontal dimension of 0.3 to 2.0 mm. The second recess 20b has a depth of 0.4 to 1.5 mm.

The first recess 20a and the second recess 20b according to the present embodiment may each have a circular, square, or rectangular opening, or an opening having another shape. The first recess 20a and the second recess 20b may each have a uniform cross section parallel to the main surface of the substrate body 20 in the depth direction. As in the cross-sectional view of FIG. 3, the first recess 20a and the second recess 20b may each have a step, or in other words have a cross section that is the same as the opening to a predetermined depth, and then have a smaller uniform cross section from the predetermined depth to the bottom. Each stepped recess as in the present embodiment has the bottom on which the light emitter or the light receiver is mountable, and a step surface on which the connection terminal for electrically connecting to the light emitter or the light receiver is to be placed.

The ground via conductors 21 are connected to a ground potential. One or more ground via conductors 21 are located outward from the first recess 20a and the second recess 20b in the substrate body 20 in a plan view. The ground via conductors 21 include multiple feedthrough conductors connected together in the thickness direction of the substrate body 20. The feedthrough conductors extend through the dielectric layers included in the substrate body 20 in the thickness direction. In the present embodiment, the ground via conductors 21 extend through the entire substrate body 20 in the thickness direction as shown in, for example, FIG. 2. In a plan view, the feedthrough conductors in the dielectric layers are located at the same positions. More specifically, the ground via conductors 21 extend linearly through the substrate body 20 from one main surface (first main surface) to its other main surface (second main surface). Each ground via conductor 21 has a first end face 21a exposed on the first main surface of the substrate body 20, and a second end face 21b exposed on the second main surface of the substrate body 20.

Each ground via conductor 21 has the first end face 21a connected to the ground conductor layer arranged on the lid 3 with the frame-shaped ground conductor layer 22 (described later). The ground via conductors 21 have the second end faces 21b connected to the external connection terminals 24 arranged on the second main surface of the substrate body 20. The ground conductor layer arranged on the lid 3 and the frame-shaped ground conductor layer 22 are electrically connected together by the ground via conductors 21 and have the same ground potential.

When a human finger, which is an example of a measurement object, touches the measurement sensor including the measurement sensor package 1 for measuring blood flow, electric charge from the human finger flows through the ground via conductors 21 from the first main surface of the substrate 2 to the lower main surface of the substrate 2 is discharged outside However, in a known structure including no ground via conductors 21, electric charge from a human enters signal wiring conductors through, for example, a bonding wire, which is an example of a connector for electrically connecting the measurement sensor package 1 to the light emitter or the light receiver, and generates noise.

In the present embodiment, the ground via conductors 21 define a path that allows electric charge from a human to easily flow in the measurement sensor package 1 to guide the electric charge on the path and discharge the electric charge outside. The structure according to the present embodiment thus prevents the electric charge from entering the signal wiring conductors.

In the present embodiment, the ground via conductors 21 are arranged along the contour of the substrate body 20. The substrate body 20 has a rectangular contour, and the ground via conductors 21 are arranged along the rectangle. More specifically, the ground via conductors 21 are spaced equally from each side of the substrate body 20 defining its contour line. In the plan view of FIG. 1, the ground via conductors 21 are drawn with dotted circles. For example, three ground via conductors 21 shown in the cross-sectional view of FIG. 2 are arranged at equal distances in the horizontal direction in an upper part of FIG. 1. The virtual straight line connecting the centers of the ground via conductors 21 extends parallel to the long sides of the substrate body 20. The other ground via conductors 21 are also arranged similarly. For example, two ground via conductors 21 vertically arranged in a left portion of FIG. 1 are arranged to have the virtual straight line connecting the centers of the ground via conductors 21 parallel to the short sides of the substrate body 20. Two ground via conductors 21 arranged horizontally in a lower part of FIG. 1 are arranged to have the virtual straight line connecting the centers of the ground via conductors 21 parallel to the long sides of the substrate body 20.

In the present embodiment, the five ground via conductors 21 in total are arranged along the rectangular contour of the substrate body 20 outward from and to surround the first recess 20a and the second recess 20b. The ground via conductors 21 are arranged at three of the four corners of the rectangle excluding one corner.

The ground via conductors 21 are arranged based on the distances from the first recess 20a and the second recess 20b. As described above, the ground via conductors 21 transmit unintended electric charge that would generate noise when entering the signal wiring conductors. In this structure, each ground via conductor 21 and the signal wiring conductor 23 (including a conductor included in the substrate body 20 and a bonding wire) formed in the measurement sensor package 1 are spaced from each other by at least a predetermined distance to prevent unintended electric charge from entering the signal wiring conductor 23 from the ground via conductors 21.

The ground via conductors 21 may not be arranged at any corner spaced by a distance shorter than a predetermined distance from the first recess 20a or the second recess 20b or in other words by a distance shorter than a predetermined distance from the signal wiring conductors 23, among the four corners of the rectangle in the present embodiment. In the present embodiment, the ground via conductor 21 is not arranged at one corner spaced by a distance shorter than a predetermined distance from the signal wiring conductor 23.

As described above, each ground via conductor 21 may have low electric resistance to guide unintended electric charge out of the package, and may have a larger diameter to have low electric resistance. However, any ground via conductor 21 having an excessively large diameter may be so close to the signal wiring conductor as to allow unintended electric charge to enter the signal wiring conductor through the ground via conductor 21. Considering these, each ground via conductor 21 may have a diameter D of, for example, 10 to 500 µm.

The frame-shaped ground conductor layer 22 is on the first main surface of the substrate body 20 to surround the openings of the first recess 20a and the second recess 20b. The frame-shaped conductor layer electrically connected to the first end faces 21a of the ground via conductors 21 exposed on the first main surface of the substrate body 20. To bond the lid 3 to the substrate 2, the frame-shaped ground conductor layer 22 is bonded to the ground conductor layer 4 using a molten-metal-based bond such as solder, Au—Sn, or a brazing material, or a resin-based bond such as an epoxy resin, a silicone resin, a thermoplastic resin, an anisotropic electroconductive resin, an electroconductive epoxy resin, or an electroconductive silicone resin.

The multiple ground via conductors 21 are arranged along the rectangular contour of the substrate body 20, and the first end faces 21a are exposed on the first main surface of the substrate body 20 along the rectangular contour of the substrate body 20. In the present embodiment, as shown in FIG. 1, the frame-shaped ground conductor layer 22 to be electrically connected to the first end faces 21a is rectangular in correspondence with the arrangement positions of the first end faces 21a. The frame-shaped ground conductor layer 22 includes lands 22a, which are connected to the first end faces 21a of the ground via conductors 21, and linear connectors 22b connecting the lands 22a. Each land 22a is larger than the first end face 21a of the corresponding ground via conductor 21 for secure connection to the first end face 21a with low resistance. For example, each land 22a has a width or a diameter of 1×D to 3×D (one to three times the diameter), where D is the diameter of the first end face 21a of the corresponding ground via conductor 21. The linear connectors 22b are thinner than the lands 22a and have a uniform width.

Each signal wiring conductor 23 is electrically connected to the light emitter or the light receiver to transmit electric signals input to the light emitter or output from the light receiver. Each signal wiring conductor 23 according to the present embodiment includes a bonding wire, which is a connector connected to the light emitter or the light receiver, a connection pad 23a to which the bonding wire is connected, signal via conductors 23c, which are electrically connected to the connection pad 23a and extend linearly from immediately below the connection pads to the second main surface of the substrate body 20, and an external connection terminal 24. The external connection terminal 24 is to be electrically connected to a connection terminal of an external mounting board, on which the measurement sensor including the measurement sensor package 1 is mountable, with a bond such as solder.

The frame-shaped ground conductor layer 22 and the external connection terminal 24 may be, for example, sequentially plated with a nickel layer having a thickness of 0.5 to 10 µm and a gold layer having a thickness of 0.5 to 5 µm to improve wettability with the bond such as solder and corrosion resistance.

The substrate 2, which can contain the light emitter and the light receiver and includes the ground via conductors 21 and the signal wiring conductors 23, may be a ceramic wiring board including the substrate body 20 including dielectric layers formed from a ceramic insulating material, and the ground via conductors 21 and the signal wiring conductors 23 formed from a conductive material. The substrate 2 may also be an organic wiring board including dielectric layers formed from a resin insulating material.

The substrate 2 that is a ceramic wiring board includes dielectric layers formed from a ceramic material, through which conductors are arranged. The ceramic wiring board is formed from multiple ceramic dielectric layers.

Examples of the ceramic material used for the ceramic wiring board include sintered aluminum oxide, sintered mullite, sintered silicon carbide, sintered aluminum nitride, sintered silicon nitride, and sintered glass ceramic.

The substrate 2 that is an organic wiring board includes insulating layers formed from an organic material, through which conductors are arranged. The organic wiring board is formed from multiple organic dielectric layers.

The organic wiring board may be any wiring board having dielectric layers formed from an organic material, such as a printed wiring board, a build-up wiring board, or a flexible wiring board. Examples of the organic material used for an organic wiring board include an epoxy resin, a polyimide resin, a polyester resin, an acryl resin, a phenol resin, and a fluorine-based resin.

The lid 3 is bonded to the first main surface of the substrate body 20 to cover the first recess 20a and the second recess 20b. The lid 3 is a plate of an insulating material. The lid 3 transmits light emitted from the light emitter contained in the first recess 20a, and light to be received by the light receiver contained in the second recess 20b.

The measurement sensor including the measurement sensor package 1 according to the present embodiment illuminates a finger, which is a measurement object, placed on the surface of the lid 3 with light emitted from the light emitter. The lid 3 formed from an electrically conductive material can allow, when the finger is placed on the lid 3, unintended electric charge described above accumulating in the fingertip to be discharged into the substrate 2 through the lid 3, and then generate noise. The lid 3 is formed from an insulating material, and thus does not allow unintended electric charge to flow through the lid 3.

The lid 3 transmits light applied to or scattered by a measurement object. The characteristics of the applied light and the scattered light depend on the light emitter used. The lid 3 may thus at least transmit the light emitted from the light emitter used. The lid 3 may be formed from an insulating material having a light transmittance of at least 70%, or specifically at least 90% for the wavelength of light emitted from the light emitter.

Examples of the insulating material for the lid 3 include a transparent ceramic material such as sapphire, a glass material, and a resin material. Examples of the glass material include borosilicate glass, crystallized glass, quartz, and soda glass. Examples of the resin material include a polycarbonate resin, an unsaturated polyester resin, and an epoxy resin.

The lid 3 is directly touched by a measurement object such as a finger, and thus needs a predetermined strength. The strength of the lid 3 is determined by the strength of its material and its thickness. The transparent ceramic material or glass material listed above can have sufficiently high strength when having at least a predetermined thickness. The lid 3 formed from a glass material may have a thickness of, for example, 0.05 to 5 mm.

The ground conductor layer 4 is arranged on a second main surface of the lid 3 facing the first recess 20a and the second recess 20b, which is a main surface opposite to a first main surface to be touched by the finger. The ground conductor layer 4 is connected to a ground potential. The ground conductor layer 4 has a first opening 4a, which allows passage of light emitted from the light emitter, and a second opening 4b, which allows passage of light to be received by the light receiver. The ground conductor layer 4 is thus electrically connected to the ground via conductors 21.

The ground conductor layer 4 functions as a mask having the first opening 4a and the second opening 4b to prevent unintended light from leaking out of the first recess 20a and to prevent unintended external light from entering the second recess 20b.

The ground conductor layer 4 also functions as an electromagnetic shield to prevent external electromagnetic waves from entering the first recess 20a and the second recess 20b. Electromagnetic waves entering the first recess 20a and the second recess 20b can be received by the signal wiring conductors 23, or in particular bonding wires, which can thus serve as antennas to receive the electromagnetic waves and generate noise. The ground conductor layer 4 arranged on the main surface of the lid 3 excluding the first opening 4a and the second opening 4b allows passage of light, but prevents entrance of electromagnetic waves, thus reducing noise.

The ground conductor layer 4 arranged on the lid 3 reduces susceptibility to noise, and improves the measurement accuracy.

The ground conductor layer 4 is electrically connected to the ground via conductors 21 and the frame-shaped ground conductor layer 22 and provided with the ground potential.

The ground conductor layer 4 may be formed as a metal thin film by, for example, vapor deposition, sputtering, or baking of a metal material such as metals including Cr, Ti, Al, Cu, Co, Ag, Au, Pd, Pt, Ru, Sn, Ta, Fe, In, Ni, and W or an alloy of these metals, on the surface of the lid 3 formed from a transparent ceramic material or a glass material. The ground conductor layer 4 has a thickness of, for example, 500 to 4000 Å. The ground conductor layer 4 may be a single layer or a laminate of multiple layers.

Figure 4:
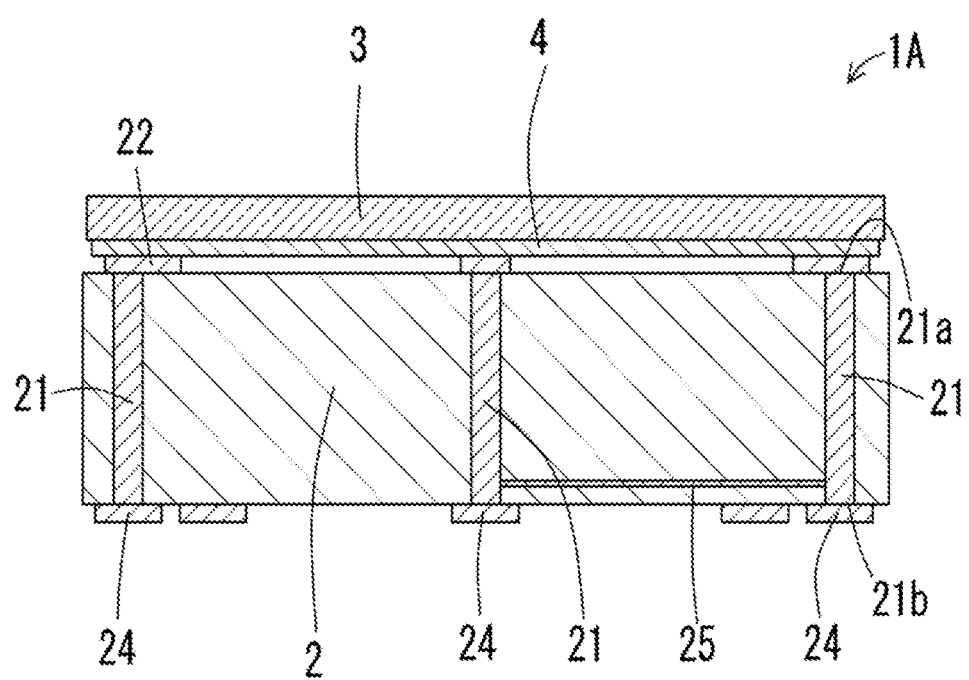
FIG. 4 is a cross-sectional view of a measurement sensor package 1A corresponding to the cross-sectional view of FIG. 2.
Figure 5:
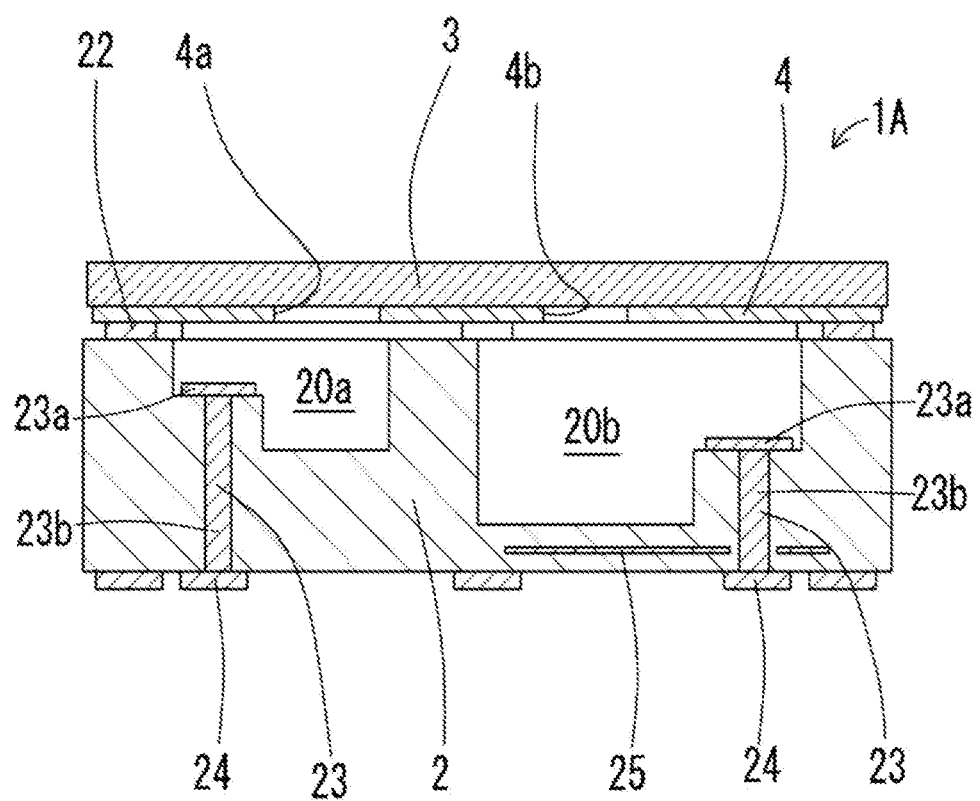
FIG. 5 is a cross-sectional view of the measurement sensor package 1A corresponding to the cross-sectional view of FIG. 3.

Other embodiments of the present invention will now be described. FIG. 4 is a cross-sectional view of a measurement sensor package 1A corresponding to the cross-sectional view of FIG. 2. FIG. 5 is a cross-sectional view of the measurement sensor package 1A corresponding to the cross-sectional view of FIG. 3.

The measurement sensor package 1A according to the present embodiment differs from the measurement sensor package 1 according to the above embodiment in that the substrate 2 further includes an internal ground conductor layer 25. The measurement sensor package 1A has the same other components. The same components are given the same reference signs as those of the measurement sensor package 1, and will not be described in detail.

The internal ground conductor layer 25 is connected to the ground potential, and arranged between the bottom of the second recess 20b and the second main surface of the substrate body 20. The internal ground conductor layer 25 is electrically connected to the ground via conductors 21 in the substrate body 20 and provided with the ground potential.

A measurement sensor used for measuring blood flow or other purposes includes a light receiver that receives a relatively small amount of light and outputs a weak electric signal. The electric signal is thus more susceptible to noise than an electric signal for controlling light emission input to the light emitter.

The measurement sensor is mounted on an external mounting board for use. An electromagnetic wave resulting from, for example, signals flowing through the wiring of the external mounting board may enter the measurement sensor package 1 from the second main surface of the substrate body 20, and may generate noise in signals flowing through the signal wiring conductors 23.

As described above, the light receiver is particularly susceptible to noise. To reduce susceptibility to noise from the external mounting board, the internal ground conductor layer 25 is arranged between the bottom of the second recess 20b, which contains the light receiver, and the second main surface. The internal ground conductor layer 25 arranged between the second recess 20b and the external mounting board functions as an electromagnetic shield.

The measurement sensor package 1A according to the present embodiment includes the internal ground conductor layer 25 to reduce susceptibility to noise and improves the measurement accuracy further.

A method for manufacturing the measurement sensor package 1 will now be described. First, the substrate 2 is formed with a method similar to a method for manufacturing a known multi-layer wiring board. For the substrate 2 that is a ceramic wiring board using alumina as a ceramic material, the powders of raw materials such as alumina ($Al_2O_3$), silica ($SiO_2$), calcium oxide (CaO), and magnesia (MgO) are mixed with an appropriate organic binder and an appropriate solvent to form slurry. The slurry is then shaped into a sheet using a known method such as a doctor blade or by calendering to obtain a ceramic green sheet (hereafter also referred to as a green sheet). The green sheet then undergoes punching into a predetermined shape. The powders of raw materials such as tungsten (W) and a glass material are mixed with an organic binder and a solvent to form a metal paste. The metal paste is then applied in a predetermined pattern by, for example, screen printing on the surface of the green sheet. The green sheet has through-holes formed and filled with the metal paste by, for example, screen printing to form via conductors. Multiple green sheets prepared in this manner are stacked on one another, and then fired together at about 1600° C. to complete the substrate 2.

The lid 3 is prepared by, for example, machining or cutting a glass material into a predetermined shape. The ground conductor layer 4, which is a metal thin film, is formed on the main surface of the lid 3 by, for example, vapor deposition, sputtering, or baking. The first opening 4a and the second opening 4b can be formed by patterning the metal thin film by, for example, photolithography (wet etching) or dry etching.

Figure 6:
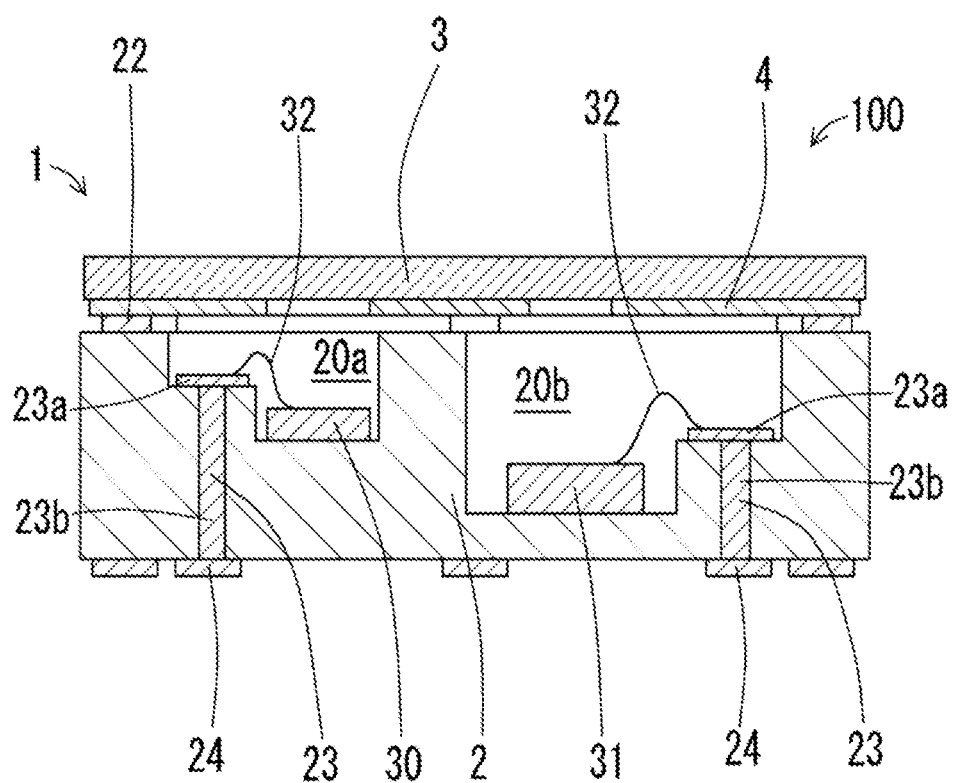
FIG. 6 is a cross-sectional view of the structure of a measurement sensor 100.

A measurement sensor 100 according to another embodiment of the present invention will now be described. FIG. 6 is a cross-sectional view of the measurement sensor 100 showing its structure. The measurement sensor 100 includes the measurement sensor package 1 or 1A, a light emitter 30, which is contained in a first recess 20a, and a light receiver 31, which is contained in a second recess 20b. The measurement sensor 100 is obtained by mounting the light emitter 30 and the light receiver 31 on the measurement sensor package 1 and connecting the light emitter 30 and the light receiver 31 to the connection pads 23a both using bonding wires 32, and joining the lid 3 to the substrate body 20.

The light emitter 30 may be formed from a semiconductor laser element such as a vertical cavity surface emitting laser (VCSEL). The light receiver 31 may be formed from a photodiode such as a silicon photodiode, a GaAs photodiode, an InGaAs photodiode, or a germanium photodiode. The light emitter 30 and the light receiver 31 may be appropriately selected in accordance with the type of a measurement object or the parameters to be measured.

For example, a VCSEL that can emit a laser beam with a wavelength of 850 nm may be used as the light emitter 30 for measuring blood flow using the optical Doppler effect. To measure another object, another device that emits a laser beam with a wavelength appropriate for the measurement object may be selected as the light emitter 30. With a laser beam emitted from the light emitter 30 and having its wavelength unchanged, any light receiver that can receive such a beam may be used as the light receiver 31. With a laser beam emitted from the light emitter 30 and having its wavelength changed, any light receiver that can receive such a beam with its wavelength changed may be used as the light receiver 31.

Although the light emitter 30 and the light receiver 31 are electrically connected to the connection pad 23a with, for example, the bonding wires 32 in the present embodiment, the connection may be achieved with another method, such as flip chip connection, a method using bumps, or a method using an anisotropic conductive film.

The measurement sensor 100 is mounted on an external mounting board for use. For example, a control unit for controlling light emission of the light emitter 30, and an arithmetic unit that calculates the blood flow rate and other parameters based on signals output from the light receiver 31 are also mounted on the external mounting board.

To start measurement, the fingertip of a finger, which is a measurement object, is placed into contact with the surface of the lid 3, and a light emitter control current is input from the external mounting board into the measurement sensor 100 through the external connection terminal 24, and input to the light emitter 30 through a signal via conductor 23b and the connection pad 23a. Light for measurement is then emitted from the light emitter 30. When the emitted light passes through a first opening 4a and is applied to the fingertip through the lid 3, the light is scattered by blood cells in the blood. When receiving the scattered light transmitted through the lid 3 and passing through a second opening 4b, the light receiver 31 outputs an electric signal corresponding to the amount of received light. The output signal then passes through the connection pad 23a and the signal via conductor 23b, and is output from the measurement sensor 100 to the external mounting board through the external connection terminal 24.

In the external mounting board, a signal output from the measurement sensor 100 is input to the arithmetic element, which can then calculate the blood flow rate based on, for example, the frequency of the illuminating light emitted from the light emitter 30 and the frequency of the scattered light received by the light receiver 31.

In the above structure, the ground via conductors 21 vertically extend linearly in the substrate body 20. The ground via conductors 21 may not extend linearly, and may be displaced inside the substrate body 20 due to, for example, an inner layer wire or the internal ground conductor layer 25 when the substrate body 20 has the first main surface electrically connected to the external connection terminals 24 on the second main surface.

In the present embodiment, the frame-shaped ground conductor layer 22 may be optional. The ground conductor layer 4 on the lid 3 and the ground via conductors 21 may be directly joined together for electrical connection between them.

The internal ground conductor layer 25 may further extend in the plane direction from a portion between the bottom of the second recess 20b and the second main surface of the substrate body 20 and may be located between the bottom of the first recess 20a and the second main surface.

Examples

A measurement sensor package (using dielectric layers formed from alumina and being 3 mm long, 4.5 mm wide, 1.2 mm thick) having the same structure as the measurement sensor package 1 shown in FIGS. 4 and 5 is prepared, and a vertical cavity surface emitting laser (VCSEL) with near-infrared wavelengths as the light emitter 30, and a silicon photodiode with a light receiving diameter of φ200 μm as the light receiver 31 are mounted on the measurement sensor package to obtain a measurement sensor according to an example of the present invention.

A measurement sensor according to a comparative example is prepared in the same manner as in the example, except that the sensor includes no ground via conductor 21.

Using each of the measurement sensors in the example and the comparative example, a signal (power spectrum) output from the light emitter with no fingertip touching the lid 3, and a signal (power spectrum) output from the light emitter with a fingertip touching the lid 3 were measured. The method for measuring the power spectrum will be described. The output signal is a current generated when an object to be measured is illuminated with light emitted from the VCSEL and a photodiode receives the resultant diffused light. The output signal is extremely weak, and is amplified with an amplifier circuit. The resultant signal then undergoes analog-digital (AD) conversion. The resultant digital signal then undergoes Fourier transformation to determine the power spectrum.

Figure 7A:
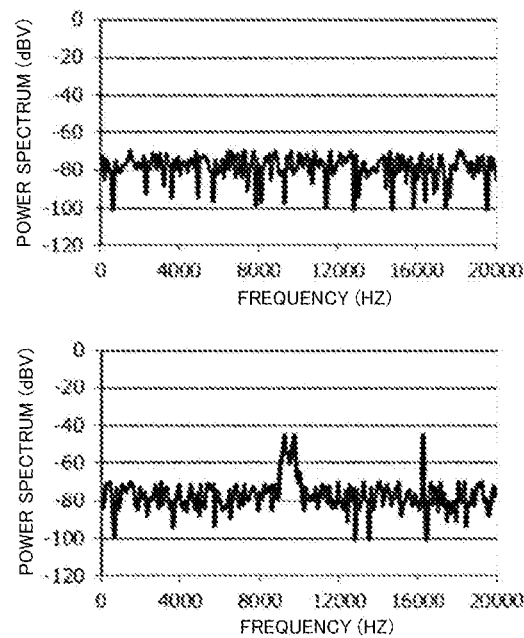
FIGS. 7A and 7B are graphs showing the measurement results of power spectra in an example and a comparative example.
Figure 7B:
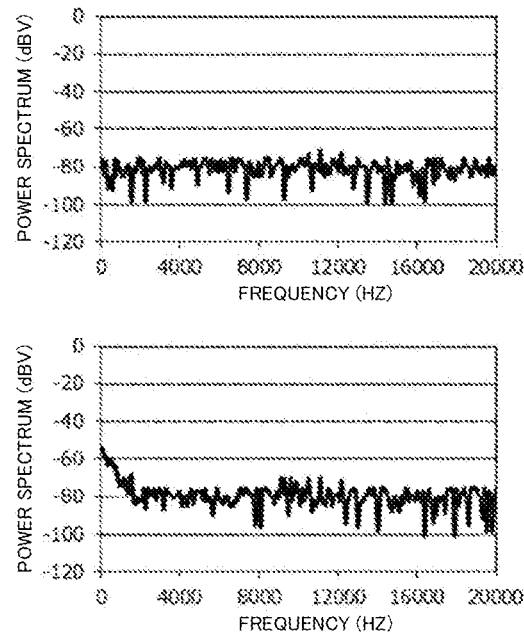

FIGS. 7A and 7B are graphs showing the measurement results of power spectra in the example and the comparative example. FIG. 7A shows the results in the comparative example, and FIG. 7B shows the results in the example. In both the example and the comparative example, the upper graph shows the results obtained without a fingertip touching the lid 3, whereas the lower graph shows the results obtained with a fingertip touching the lid.

As in the upper graphs in FIGS. 7A and 7B, no noise occurs when a fingertip is not touching the lid 3 in the example and the comparative example.

As in the lower graph in FIG. 7A, in the comparative example without the ground via conductor 21, noise occurs at frequencies of about 9 to 10 kHz, and about 16 kHZ when a fingertip is touching the lid 3. No change is observed in the output at less than 2 kHz due to scattering by blood flow to be otherwise detected.

In the example using the ground via conductors 21, no noise occurs unlike in the comparative example, and a change in the output is observed at less than or equal to 2 kHz, as shown in the lower graph in FIG. 7B.

Figure 8:
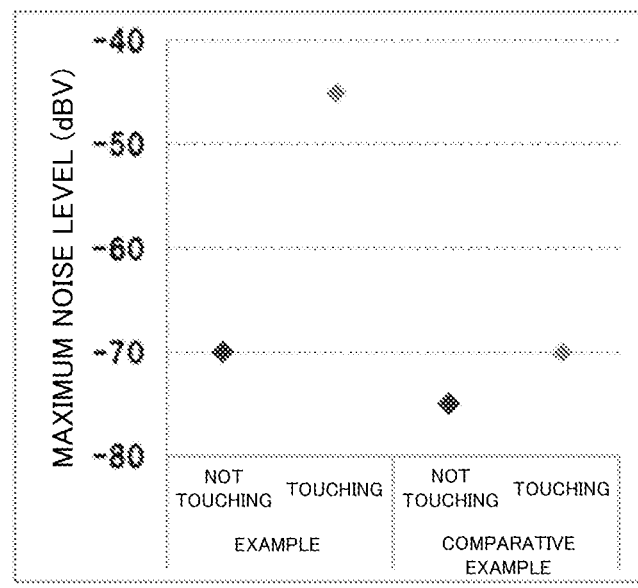
FIG. 8 is a graph showing the evaluation results in the example and the comparative example.

FIG. 8 is a graph showing the evaluation results in the example and the comparative example. The maximum noise level was used as the evaluation results. The maximum noise level is calculated by subtracting the maximum output value and the minimum output value at frequencies greater than or equal to 2 kHz in the power spectrum. Noise is more notable as the maximum noise level increases, whereas less noise is generated as the minimum noise level is lower.

As shown in FIG. 8, the maximum noise level is small both in the example and the comparative example when a fingertip is not touching the lid 3. Additionally, the maximum noise level in the example is smaller than the maximum noise level in the comparative example, revealing that the structure of the example reduces even slight noise occurring when a fingertip is not touching the lid 3. When a fingertip is touching the lid 3, the maximum noise level increases only slightly in the example, whereas the maximum noise level increases in the comparative example as compared with when a fingertip is touching the lid 3.

As described above, the structure of the example including the ground via conductors 21 reduces noise generated from a touch of an object to be measured, and enables highly accurate measurement of blood flow.

The present invention may be embodied in various forms without departing from the spirit or the main features of the present invention. The embodiments described above are thus merely illustrative in all respects. The scope of the present invention is defined not by the description given above but by the claims, and any modifications and alterations contained in the claims fall within the scope of the present invention.

REFERENCE SIGNS LIST 1, 1A measurement sensor package
2 substrate
3 lid
4 ground conductor layer
4a first opening
4b second opening
20 substrate body
20a first recess
20b second recess
21 ground via conductor
21a first end face
21b second end face
22 frame-shaped ground conductor layer
22a land
22b linear connector
23 signal wiring conductor
23a connection pad
23b signal via conductor
24 external connection terminal
25 internal ground conductor layer
30 light emitter
31 light receiver
32 bonding wire
100 measurement sensor

The invention claimed is:

1. A measurement sensor package, comprising:
a substrate including
a substrate body including a plurality of dielectric layers stacked on one another, the substrate body being a rectangular plate and including a first recess and a second recess on a first surface thereof, the first recess being configured to contain a light emitter, the second recess being configured to contain a light receiver, and one or more ground via conductors located outward from the first recess and the second recess included in the substrate body in a plan view, the one or more ground via conductors being connectable to a ground potential;
a lid being a plate covering the first recess and the second recess, the lid comprising an insulating material, the lid being configured to transmit light emitted from the light emitter contained in the first recess and to transmit light to be received by the light receiver contained in the second recess; and
a ground conductor layer located on a surface of the lid facing the first recess and the second recess and connectable to the ground potential, the ground conductor layer having a first opening configured to allow passage of light emitted from the light emitter, and a second opening configured to allow passage of light to be received by the light receiver, the ground conductor layer being electrically connectable to the one or more ground via conductors,
wherein
the first recess comprises a first bottom facing the lid and the second recess comprises a second bottom facing the lid,
the first bottom is configured to mount the light emitter and the second bottom is configured to mount the light receiver,
the one or more ground via conductors comprise a plurality of ground via conductors included in the substrate,
the plurality of ground via conductors are arranged along a perimeter of the first surface of the substrate body, and each of the plurality of ground via conductors has a first end face exposed on the first surface of the substrate body,
the substrate includes a frame-shaped ground conductor layer surrounding an opening of the first recess and an opening of the second recess on the first surface of the substrate body, and the frame-shaped ground conductor layer is configured to be electrically connected to the first end face of each of the plurality of ground via conductors, and
the frame shaped ground conductor layer is a plate with a hole in a center such that the frame shaped ground conductor layer surrounds the opening of the first recess and the opening of the second recess.

2. The measurement sensor package according to claim 1, wherein the substrate includes an inner ground conductor layer located between the second bottom and a second surface of the substrate body opposite to the first surface, and the inner ground conductor layer is connectable to the ground potential.

3. The measurement sensor package according to claim 2, wherein the dielectric layers contain a ceramic material.

4. The measurement sensor package according to claim 1, wherein the dielectric layers contain a ceramic material.

5. The measurement sensor package according to claim 1, wherein the first recess and the second recess each contain a connection pad.

6. The measurement sensor package according to claim 5, wherein
the connection pad in the first recess is on a step, and the step is at a different depth than the first bottom.

7. The measurement sensor package according to claim 5, wherein
the connection pad in the second recess is on a step, and the step is at a different depth than the second bottom.

8. The measurement sensor package according to claim 1, wherein the frame shaped ground conductor layer includes a plurality of lands, and each of the lands is connected to the first end face of each of the ground via conductors.

9. The measurement sensor package according to claim 8, wherein a width of each of the lands is equal to or greater than a width of the first end face that is connected to the land.

10. The measurement sensor package according to claim 1, wherein the frame shaped ground conductor layer is sequentially plated with a nickel layer and a gold layer.

11. The measurement sensor package according to claim 10, wherein the nickel layer has a thickness of 0.5 to 10 µm.

12. The measurement sensor package according to claim 10, wherein the gold layer has a thickness of 0.5 to 5 µm.

13. A measurement sensor, comprising:
the measurement sensor package according to claim 1;
a light emitter contained in the first recess; and
a light receiver contained in the second recess.

\* \* \* \* \*